US00PP09672P

United States Patent [19]

Olij

[11] Patent Number: Plant 9,672

[45] Date of Patent: Oct. 29, 1996

[54] HYBRID TEA ROSE PLANT NAMED 'OLIJKROFT'

[75] Inventor: Huibert W. Olij, De Kwakel, Netherlands

[73] Assignee: The Conard-Pyle Company, West Grove, Pa.

[21] Appl. No.: 544,392

[22] Filed: Oct. 17, 1995

[51] Int. Cl.[6] ..... A01H 5/00

[52] U.S. Cl. ..... Plt./11

[58] Field of Search ..... Plt./11, 15, 22

[56] References Cited

U.S. PATENT DOCUMENTS

P.P. 2,997 11/1970 Warriner ..... Plt./11

P.P. 5,040 4/1983 Warriner ..... Plt./11

P.P. 5,901 3/1987 Warriner ..... Plt./11

P.P. 6,261 8/1988 Olesen et al. ..... Plt./8.2

*Primary Examiner*—Howard J. Locker

*Attorney, Agent, or Firm*—Burns, Doane, Swecker & Mathis, L.L.P.

[57] ABSTRACT

A new and distinct variety of Hybrid Tea rose plant is provided which abundantly forms attractive long-lasting bicolored blossoms that are light yellow and lightly edged with red. The plant exhibits an erect growth habit and strong vegetation. The new variety exhibits good disease resistance and is particularly well suited for cut flower production under greenhouse growing conditions.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was the 'Texas' variety (non-patented in the United States). The male parent (i.e., the pollen parent) was 'Belle Blonde' variety (non-patented in the united States). The parentage of the new variety can be summarized as follows:

'Texas'×'Belle Blonde'.

The seeds resulting from the above pollination were sown and 14 small plants were obtained which were physically and biologically different from each other. Selective study resulted in the identification of a single plant of the new variety.

It was found that the new variety of Hybrid Tea rose plant of the present invention possesses the following combination of characteristics (a) forms in abundance attractive bicolored blossoms that are light yellow and lightly edged with red,
(b) exhibits an erect growth habit,
(c) is well suited for cut flower production under greenhouse growing conditions, and
(d) exhibits good disease resistance.

The new variety well meets the needs of the horticultural industry and is particularly well suited for the commerical production of cut flowers while growing indoors.

The new variety has been found to undergo asexual propagation in France by a number of routes, including budding, grafting, and cuttage. Asexual propagation by the above-mentioned techniques in France has shown that the characteristics of the new variety are stable and are strictly transmissible by such asexual propagation from one generation to another.

The new variety has been named the 'Olijkroet' Variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during November while budded on *Rosa indica* understock and growing in greenhouses at Le Cannet des Maures, Var, France.

FIG. 1 — illustrates a specimen of a young shoot;

FIG. 2 — illustrates a specimen of a flower in the course of opening;

FIG. 3 — illustrates a specimen of an open flower — plan view — obverse;

FIG. 4 — illustrates a specimen of an open flower — plan view — reverse;

FIG. 5 — illustrates a specimen of a fully open flower — plan view — obverse;

FIG. 6 — illustrates a specimen of a fully open flower — plan view — reverse;

FIG. 7 — illustrates a specimen of a floral receptacle showing the arrangement of the stamens and pistils and the typical configuration of the sepals;

FIG. 8 — illustrates a specimen of a floral receptacle showing the arrangement of the pistils (stamens removed);

FIG. 9 — illustrates a specimen of a flowering stem;

FIG. 10 — illustrates a specimen of a main branch;

FIG. 11 — illustrates a specimen of a leaf with three leaflets — plan view — upper surface.

FIG. 12 — illustrates a specimen of a leaf with five leaflets — plan view — under surface; and FIG. 13 — illustrates a specimen of a leaf with seven leaflets — plan view — upper surface.

DETAILED DESCRIPTION

Figures 1, 2, 3, 4, 5, 6, 7, 8, 9, 10, 11, 12, 13:
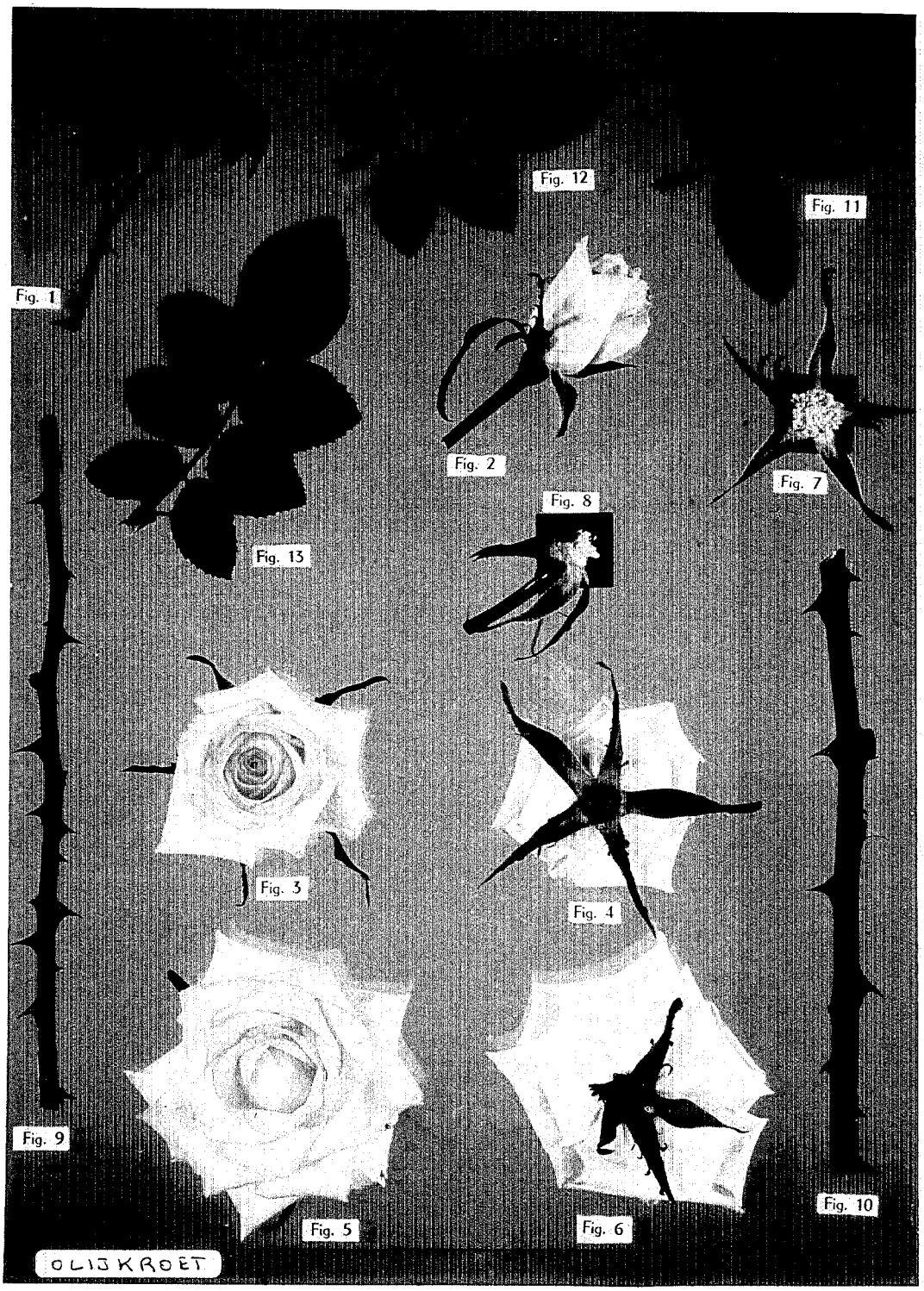

The chart used in the identification of the colors is that of the Royal Horticultural Society (R.H.S. Colour Chart). The description is based on the observation during September of three year-old plants while budded on *Rosa indica* understock and growing in greenhouses at Le Cannet des Maures, Var, France. The coloration in common terms precedes reference to the chart.

Class: Hybrid Tea.

Plant:

*Height.*—Approximately 40 to 70 cm. on average at the end of the growing season.

*Habit.*—Erect.

Branches:

*Color.*—Young stems: medium green, Green Group 143B. Adult wood: medium green, Green Group 137A.

Thorns.—Size: medium. Quantity: numerous. Color: greenish on young stems and tan on adult wood (as illustrated).

Leaves:

*Stipules.*—Adnate, pectinate, narrow and linear.

*Petioles.*—Upper surface: striped reddish brown on young foliage and medium green on adult foliage. Under surface: light green.

*Leaflets.—Number: commonly* 3, 5 (most often), and 7. Shape: elliptic. Serration: single and regular. Texture: consistent. General apearance: dense, medium green in coloration, and semi-bright. Color (young foliage): upper surface: medium green, Yellow-Green Group 146B, and more or less stained with brownish coloration. under surface: medium green, Yellow-Green Group 146B, and stained with reddish-brown coloration. Color (adult foliage): upper surface: medium green, Green Group '137A. under surface: medium green, Green Group 137C.

Inflorescence:

*Number of flowers.*—Usually one to three per stem.

*Peduncle.*—Medium green in coloration and smooth. The length is approximately 10 cm. on average.

*Sepals.*—Upper surface: tomentose, and greenish in coloration. Under surface: light green in coloration and commonly with many appendiculate edges.

*Buds.*—Shape: conical. Length: approximately 3 cm. on average. Size: large. Color upon opening: upper surface: Sulphur Yellow, Yellow Group 6B, and lightly edged with red, Red Group 42B. under surface: Chartreuse Green, Yellow-Green Group 154B, and lightly edged with red, Red Group 42B.

*Flower.*—Shape: cup-shaped with a deep center. Diameter: approximately 12 to 13 cm. on average. Color (when opening begins): upper surface: Canary Yellow, Yellow Group 9B, and edged with red, Red Group 42C. under surface: Dresden Yellow, yellow Group 5C, and edged with red, Red Group 42C. Color (when blooming): upper surface: Canary Yellow, Yellow Group 9C, and edged with red, Red Group 42C. under surface: Mimosa Yellow, Yellow Group 8C, and lightly edged with red, Red Group 42C. Color (at end of opening): upper surface: Canary Yellow, Yellow Group 9C, and lightly edged with red, Red Group 42C. under surface: Mimosa Yellow, Yellow Group 8C, and lightly edged with red, Red Group 42C. Fragrance: none. Lasting quality: very good. Petal shape: generally oval at the tip and obtuse at the base. Petal drop: good. Stamen number: approximately 68 on average. Anthers: normal golden yellow in coloration. Filaments: yellowish in coloration. Pistils: approximately 82 on average. Stigmas: yellowish in coloration. Styles: yellowish-green in coloration. Receptacle: medium green in coloration, smooth, and in longitudinal section in the shape of a wide pitcher.

Development:

*Vegetation.*—Strong.

*Blooming.*—Abundant.

*Resistance to diseases.*—Good.

I claim:

1. A new and distinct variety of Hybrid Tea rose plant characterized by the following combination of characteristics:

(a) forms in abundance attractive bicolored blossoms that are light yellow and lightly edged with red,
(b) exhivits an erect growth habit,
(c) is well suited for cut flower production under greenhouse growing conditions, and
(d) exhibits good disease resistance;

sustantially as herein shown and described.

* * * * *

OLIJKROET